United States Patent
Takano et al.

(10) Patent No.: US 8,052,898 B2
(45) Date of Patent: Nov. 8, 2011

(54) HYDROGEN GAS DETECTING MATERIAL AND THE COATING METHOD

(75) Inventors: Katsuyoshi Takano, Takasaki (JP); Shunya Yamamoto, Takasaki (JP); Aichi Inouye, Takasaki (JP); Masaki Sugimoto, Takasaki (JP); Masahito Yoshikawa, Takasaki (JP)

(73) Assignee: Japan Atomic Energy Agency, Ibaraki (JP)

( * ) Notice: Subject to any disclaimer, the term of this patent is extended or adjusted under 35 U.S.C. 154(b) by 224 days.

(21) Appl. No.: 12/225,815

(22) PCT Filed: Apr. 4, 2007

(86) PCT No.: PCT/JP2007/057600
§ 371 (c)(1),
(2), (4) Date: Sep. 30, 2008

(87) PCT Pub. No.: WO2007/116919
PCT Pub. Date: Oct. 18, 2007

(65) Prior Publication Data
US 2009/0267032 A1    Oct. 29, 2009

(30) Foreign Application Priority Data
Apr. 4, 2006   (JP) ................. 2006-102809

(51) Int. Cl.
*G02B 5/23* (2006.01)
*B24B 1/00* (2006.01)
*B24B 7/19* (2006.01)
*B24B 7/30* (2006.01)

(52) U.S. Cl. .............. 252/586; 204/298.02; 423/606; 428/220; 451/41

(58) Field of Classification Search ............ 252/586; 204/298.02; 423/606; 428/220; 451/6, 41
See application file for complete search history.

(56) References Cited

U.S. PATENT DOCUMENTS
2004/0023595 A1 * 2/2004 Ping et al. ............... 451/6

FOREIGN PATENT DOCUMENTS
| JP | 60-40945 | 3/1985 |
| JP | 60-211348 | * 10/1985 |
| JP | 61-201143 | 9/1986 |
| JP | 4-279681 | 10/1992 |
| JP | 7-72080 | 3/1995 |
| JP | 8-253742 | 10/1996 |
| JP | 10-10048 | 1/1998 |
| JP | 2005-233740 | 9/2005 |
| JP | 2005-345338 | 12/2005 |

OTHER PUBLICATIONS

Wenyi Zhang, et al., "A novel semiconductor NO gas sensor operating at room temperature", *Sensors and Actuators*, 1998, vol. B49, No. ½, pp. 58-62.
International Search Report mailed on Jun. 12, 2007 in connection with International Application No. PCT/JP2007/057600.
Yonsu O et al., "Hikari Kenchisiki Suiso Gas Sensor no Sakusei to Hyoka I. Pd/WO$_3$ Soshi no Kurikaeshi Kenchi Tokusei", 1992, The Ceramic Society of Japan, Nenkai Koen Yokoshu, p. 240.
International Search Report mailed Jun. 12, 2007 in corresponding International Patent Application PCT/JP2007/057600.

* cited by examiner

*Primary Examiner* — Ling Choi
*Assistant Examiner* — Bijan Ahvazi

(57) ABSTRACT

A hydrogen gas detecting material, which changes in light absorption characteristics when exposed to an atmosphere containing hydrogen, and the coating method are characterized in that (1) the principal component of the hydrogen gas detecting material is tungsten oxide, (2) palladium is deposited on the surface of the tungsten oxide, (3) the tungsten oxide is coated on a substrate by a sputtering method involving a controlled oxygen pressure, and (4) the temperature of the substrate during coating with the tungsten oxide is room temperature (20° C.).

6 Claims, 2 Drawing Sheets

HYDROGEN GAS DETECTING MATERIAL AND THE COATING METHOD

CROSS REFERENCE TO RELATED APPLICATIONS

This application claims the benefit under 35 U.S.C. Section 371 of International Application No. PCT/JP2007/057600, filed Apr. 4, 2007, which claimed priority to Japanese Application No. 2006-102809, filed Apr. 4, 2006 in the Japanese Patent Office, the disclosures of which are hereby incorporated by reference.

TECHNICAL FIELD

This invention relates to a hydrogen gas detecting material using tungsten oxide, and the coating method.

BACKGROUND ART

In recent years, global warming due to the emission of greenhouse gases ($CO_2$, etc.) associated with mass consumption of fossil fuels has posed a problem. In response, the realization of an energy supply system relying minimally on fossil fuels has been necessitated. A system for electric power supply by a hydrogen fuel cell, in particular, is an electric power supply system which does not discharge $CO_2$ as an environmental load. Technologies for its coating are under study in many fields as an infrastructure for realizing hydrogen society aimed at sustained development. However, hydrogen as a fuel is a combustible gas involving explosion, and its handling requires a careful safety monitor. For this purpose, the development of an inexpensive detecting method, which safely detects leaking trace hydrogen, becomes one of the most important challenges in realizing hydrogen society. The trace of leaking hydrogen has hitherto been monitored using a hydrogen detector, or by confirming the amount of hydrogen consumption. However, prompt pinpointing of the location of leakage is difficult. Much labors and time are usually spent on the pinpointing. The general hydrogen gas detector measures a change in electrical resistance on the surface of a semiconductor due to the adsorption of hydrogen. Since an explosion is caused by ignition of hydrogen at the power circuit in general hydrogen gas detector, it has been problematic in terms of safety. Under these circumstances, proposals have been made for hydrogen leakage detecting methods (have been proposed) in which hydrogen leakage detecting paints containing fine particles (particle size: 1 μm or less) comprising palladium oxide or tungsten oxide, or hydrogen gas detecting materials coated with such paints are applied or stuck to a location suspected of hydrogen leakage (Patent Documents 1 to 3). Judgment of hydrogen leakage by the paint is based on the visual confirmation of the site of discoloration of palladium oxide or tungsten oxide by the adsorption of leaking hydrogen. Thus, this method is a hydrogen leakage detecting method which facilitates pinpointing of the location of leakage and has high safety.

However, the paint is applied as a film by a chemical manufacturing process using wide varieties of chemicals, including a strongly acidic aqueous solution, a strongly basic aqueous solution, and a harmful organic solvent. Thus, its manufacturing cost is high, and it is also problematical in terms of load on the surrounding environment and environmental sanitation for an operator. In recent years, moreover, there has been a concern about the effect on humans of inhalation of, or exposure to, fine particles with a particle size of 1 μm or less. The production and handling of such paints are not preferred for environmental sanitation for the operator.

Patent Document 1: JP-A-4-279681
Patent Document 2: JP-A-8-253742
Patent Document 3: JP-A-2005-345338

DISCLOSURE OF THE INVENTION

Problems to be Solved by the Invention

The detecting method, in which a hydrogen leakage detecting paint, or a hydrogen gas detecting material coated with such a paint is applied or stuck to a location suspected of hydrogen leakage, is a hydrogen leakage detecting method which facilitates pinpointing of the location of a hydrogen leakage and has high safety. However, the hydrogen leakage detecting paint entails a high manufacturing cost, imposes a high environmental load, and is problematical in terms of environmental sanitation.

Means for Solving the Problems

The present invention, as a solution to the above-mentioned problems, provides a hydrogen gas detecting material comprising a thin film of tungsten oxide, and the coating method. The above hydrogen gas detecting material is characterized in that (1) its principal component is tungsten oxide and its shape is a thin film, and that (2) it has a stacked structure comprising palladium and tungsten oxide. The hydrogen gas detecting material is coated on a substrate, with the substrate temperature being room temperature (20° C.), by a sputtering method at a controlled oxygen pressure.

Advantages of the Invention

According to the present invention, it becomes possible to coat a hydrogen gas detecting material, which changes in light absorption characteristics upon hydrogen adsorption, onto the surface of a substrate comprising an organic compound, a resin, or a polymeric material such as vinyl. As a result, it becomes possible to produce a hydrogen gas detecting sheet or a hydrogen gas sensor which entails a low manufacturing cost, imposes a low environmental load, and is safe in terms of environmental sanitation.

BEST MODE FOR CARRYING OUT THE INVENTION

A method of coating a hydrogen gas detecting material using a thin film of tungsten oxide according to the present invention will now be described in more detail below.

Figure 1:
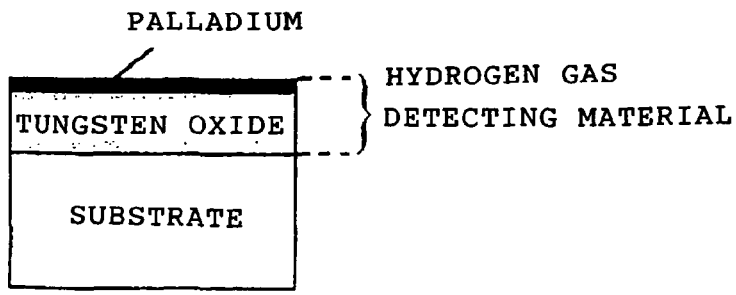
FIG. 1 is a schematic view of a section of a hydrogen gas detecting material.

The hydrogen gas detecting material of the present invention is characterized in that it is composed of a thin film of tungsten oxide, and palladium deposited on the surface of the thin film of tungsten oxide, and that the palladium adsorbs a molecular hydrogen gas to dissociate it into hydrogen atoms. An embodiment of the hydrogen gas detecting material of the present invention is shown in FIG. 1. Tungsten oxide is preferably in a thin film with a thickness of 300 nm to 1 μm. The thickness of less than 300 nm is inconvenient, because it is difficult to recognize a change in the transmitted light intensity. The thickness of more than 1 μm is inconvenient, because an exfoliation of tungsten oxide is apt to occur. The thickness of the deposited palladium is preferably 2 nm to 20 nm. If the thickness of palladium is larger than 20 nm, the quantity of incident light shielded by palladium increases, thus making a change in the transmitted light intensity difficult to recognize. This is inconvenient. If the thickness of palladium, as a catalytic metal, is 2 nm to 20 nm, a change in the transmitted light intensity is obtained which can be easily recognize, namely judged visually of hydrogen leakage is possible, thus making it possible to detect a hydrogen gas. A transparent substrate is preferably transparent or translucent to visible light of 400 nm or more. Examples of the substrate are, although not limited to, substrates composed of polymers such as polycarbonate, polyethylene, polyethylene terephthalate (PET), polypropylene, and polyvinylidene chloride. As the transparent substrate, an amorphous quartz glass substrate, for example, can be used.

Next, a description will be offered for preferred embodiments of the coating method for the hydrogen gas detecting material of the present invention. The coating method for the hydrogen gas detecting material of the present invention includes sputtering a sputtering target comprising tungsten to form a thin film of tungsten oxide on the surface of the substrate, and then depositing palladium on the surface of the thin film of tungsten oxide, and is characterized by controlling an oxygen pressure during formation of the tungsten oxide film to control light absorption characteristics attributed to adsorption of hydrogen. The purity of tungsten as the sputtering target is not limited, but is preferably high. The sputtering is preferably performed in a mixed atmosphere comprising argon and oxygen. The substrate temperature for execution of sputtering is preferably room temperature (20° C.). Detection of hydrogen leakage is determined by a visual change in color. Thus, it is preferred, as the light absorption characteristics demanded of the hydrogen gas detecting material, that a change in the transmittance due to adsorption of hydrogen be 50% or more. To achieve the above light absorption characteristics, if sputtering is performed in a mixed atmosphere comprising argon and oxygen, with the sputtering power charged being 50 W and the distance between the substrate and the target being 10 cm, for example, it is recommendable that the oxygen gas pressure be 14 to 80 mPa, and the argon gas pressure be 130 to 170 mPa. Preferably, the oxygen gas pressure is 15 to 40 mPa, and the argon gas pressure is 140 to 160 mPa. In order to achieve a transmittance change of 50% or more due to hydrogen adsorption if sputtering is performed in an argon-oxygen mixed atmosphere, it is recommendable to control the proportion of the oxygen gas to about 10% to about 30% of the total gas pressure (the sum of the oxygen gas pressure and the argon gas pressure), although this proportion, strictly, depends on other sputtering conditions as well. Thus, when the total gas pressure is set at 100 mPa if the sputtering power charged is 50 W and the distance between the substrate and the target is 10 cm, it is advisable that the partial pressure of the oxygen gas be controlled to 10 to 30 mPa. The gas pressures of the atmosphere and the other sputtering conditions can be set, as appropriate, by a person of ordinary skill in the art based on the disclosures made herein.

Deposition of palladium can be performed by radio frequency sputtering, direct current sputtering, molecular beam epitaxy, or vacuum evaporation. Any of these methods may be employed, as long as it can deposit palladium at the heat resistant temperature or lower of the substrate. If palladium is deposited by the radio frequency sputtering method, for example, this method is preferably performed under such deposition conditions that the sputtering power is 25 W to 50 W, the substrate is at room temperature, and the atmosphere has an argon gas pressure of 130 to 170 mPa. Other methods and conditions for deposition of palladium can be set, as appropriate, by a person of ordinary skill in the art based on the disclosures made herein.

EXAMPLES

Example 1

In Example 1, a thin film of tungsten oxide was coated on the surface of a quartz glass substrate 20 mm long, 20 mm wide and 0.5 mm thick, in order to evaluate the crystal structure of the coated tungsten oxide and optimize its hydrogen detecting characteristics. The tungsten oxide film was coated by using tungsten as a target and sputtering the metallic tungsten target for 30 minutes at a power of 50 W while setting the distance between the substrate and the target at 10 cm, setting the substrate temperature at room temperature, and controlling the atmosphere to have an argon gas partial pressure of 148 mPa and an oxygen partial pressure of 22 mPa. The film thickness of tungsten oxide was of the order of 0.3 μm.

Figure 2:
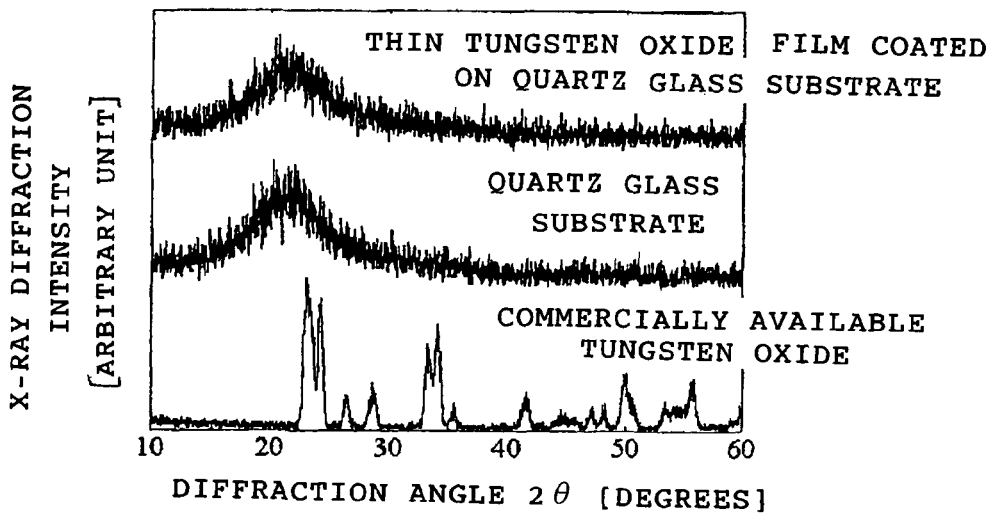
FIG. 2 shows the X-ray diffraction pattern of a thin film of tungsten oxide coated on a quartz glass substrate.

The results of evaluation of the crystallinity of the coated film by X-ray diffraction are shown in FIG. 2. A Cu Kα radiation was used as a radiation source. A diffraction peak with a large width was observed around a diffraction angle of 23 degrees, but no other peaks were seen. Comparisons with the diffraction peaks of a quartz glass substrate and commercially available tungsten oxide ($WO_3$) having a purity of 99.9% showed that the wide peak around the diffraction angle of 23 degrees originated from the amorphism of the quartz glass substrate. Thus, the resulting thin film of tungsten oxide was considered to be amorphous.

Then, palladium was deposited in a thickness of 15 nm on the thin tungsten oxide film by use of radio frequency sputtering to form a hydrogen gas detecting material. Sputtering of palladium was performed for 40 seconds with the use of metallic palladium as a target under the following conditions: electric power 50 W, and argon gas pressure 148 mPa.

Figure 3:
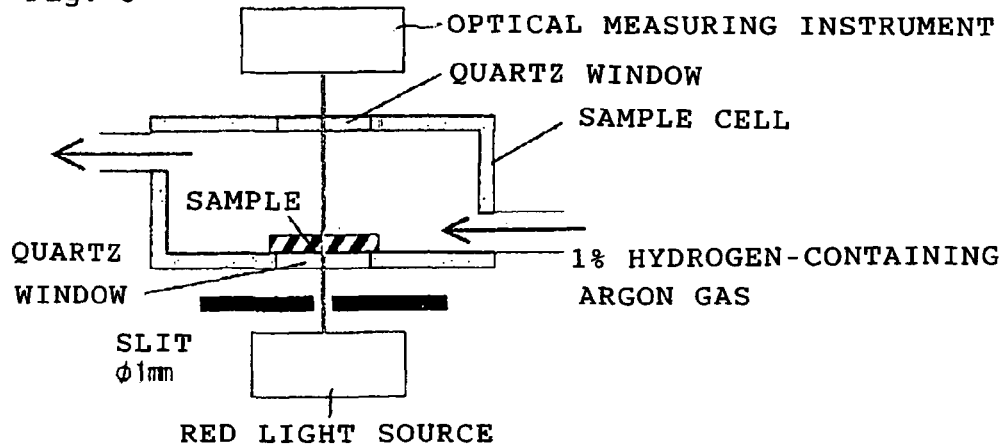
FIG. 3 shows a layout for measuring the light absorption characteristics of the hydrogen gas detecting material coated on the substrate in response to a hydrogen gas.

The light absorption characteristics of the hydrogen gas detecting material in response to hydrogen were evaluated by measuring the transmitted light intensities before and after exposure to hydrogen with the use of a measuring equipment, as shown in FIG. 3, and determining their change. The method of evaluation comprised irradiating a sample in a cell, whose atmosphere can be controlled, with red light with a wavelength of 645 nm at which the transmitted light intensity changes most remarkably, and making measurements in the following manner using a spectrometric measuring instrument:

(1) The transmitted light intensity $I_0$ of the sample before hydrogen adsorption was measured.
(2) The interior of the sample cell was gas purged for 20 minutes with hydrogen at a concentration of 1% diluted with an argon gas which was fed at a flow rate of 70 ml/min.
(3) The transmitted light intensity I of the sample after hydrogen adsorption was measured.
(4) Based on I and $I_0$, relative transmittance ($I/I_0$), i.e., a change in the transmittance of light occurring upon hydrogen adsorption compared with the level before hydrogen adsorption, was determined.

Figure 4:
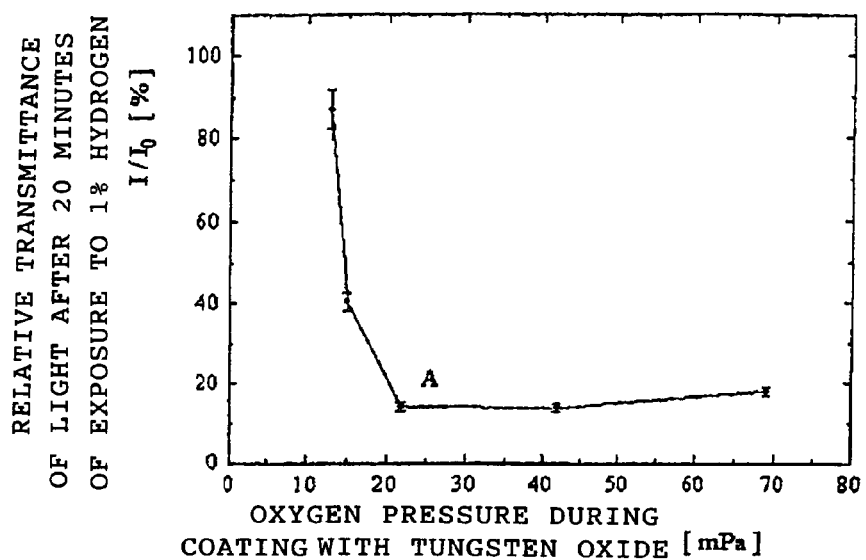
FIG. 4 shows the light absorption characteristics, in response to a hydrogen gas, of the hydrogen gas detecting material formed from tungsten oxide deposited at an oxygen pressure of 13 mPa, 15 mPa, 22 mPa (A), 42 mPa and 69 mPa.

Symbol A in FIG. 4 shows the results of the measurement of the relative transmittance of the hydrogen gas detecting material. The relative transmittance of the hydrogen gas detecting material was 14%, meaning that the change in the transmittance was 86%. This finding shows that the hydrogen gas detecting material has the performance of being able to detect hydrogen sufficiently.

Comparative Examples 1 and 2 and Examples 2 and 3

In the present invention, it is important to control the oxygen partial pressure during coating with tungsten oxide. As comparative examples for Example 1, and other examples, thin films of tungsten oxide were coated by controlling the oxygen partial pressure to various values (Comparative Example 1: 13 mPa, Comparative Example 2: 15 mPa, Example 2: 42 mPa, Example 3: 69 mPa), and equating the film thickness of tungsten oxide and the other coating conditions with those in Example 1. The results of the X-ray diffraction measurements on these films were the same as those on the thin tungsten oxide film of Example 1, demonstrating that the thin films of tungsten oxide obtained by the coating method of the present invention were amorphous. Palladium was deposited on the surface of each thin tungsten oxide film under the same conditions as in Example 1, and the light absorption characteristics in response to hydrogen were examined in the same manner as in Example 1. The relative transmittances of the hydrogen gas detecting materials are shown in FIG. 4 along with the results obtained in Example 1. When the oxygen pressure was 14 mPa or lower, the relative transmittance of the present hydrogen gas detecting material was 87%. Namely, the change in the transmittance was 13%, thus leading to difficulty in detecting hydrogen. When the oxygen pressure was higher than 14 mPa, the hydrogen gas detecting material was found to change in the transmittance by 50% or more owing to the adsorption of hydrogen. The use of the thin tungsten oxide film coated by controlling the oxygen partial pressure to higher than 14 mPa, therefore, is shown to permit hydrogen detection sufficiently.

Examples 4 to 8

Figure 5:
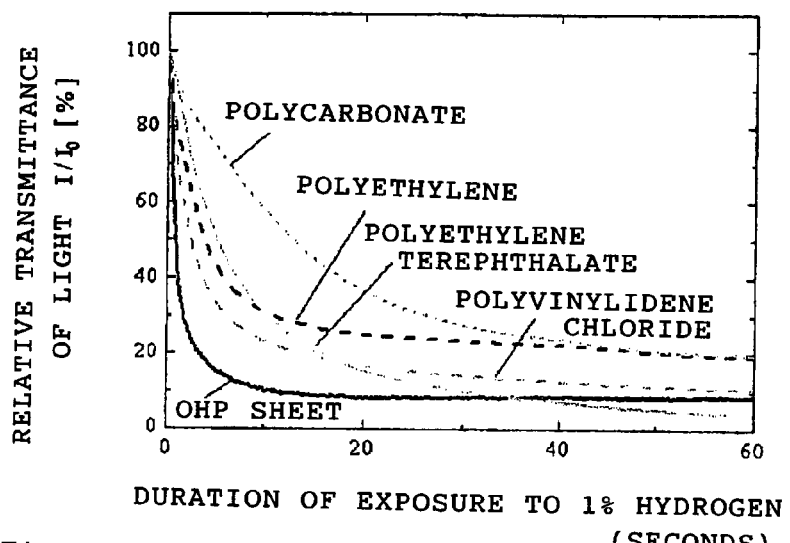
FIG. 5 shows the light absorption characteristics, in response to a 1% hydrogen gas, of the hydrogen gas detecting material coated on various substrates.

Hydrogen gas detecting materials were produced using each of a 1.2 mm thick polycarbonate plate, a 40 μm thick polyethylene sheet, a 11 μm thick polyvinylidene chloride (Saran Wrap, ASAHI CHEMICAL INDUSTRY CO., LTD.), a 100 μm thick OHP sheet (a product of Fuji Xerox Co., Ltd.), and a 100 μm thick polyethylene terephthalate (PET) sheet as a substrate, and adopting the same coating conditions as in Example 1. The hydrogen gas detecting materials were each examined for the light absorption characteristics responsive to a hydrogen gas in the same manner as in Example 1. FIG. 5 shows changes gradually in the relative transmittance of the hydrogen gas detecting material when exposed to hydrogen. The relative transmittances of the hydrogen gas detecting materials coated on polycarbonate (Example 4), polyethylene (Example 5), polyvinylidene chloride (Example 6), OHP (Example 7), and PET (Example 8), after 60 seconds of exposure to hydrogen, were 20%, 20%, 11%, 9% and 4%, respectively. These results show that the hydrogen gas detecting material using the substrate with poor heat resistance to temperatures of 100° C. or higher has the performance of being able to detect hydrogen sufficiently. From the above results, it is seen that the coating method of the present invention can coat a hydrogen gas detecting material capable of detecting hydrogen, no matter what the kind of the substrate is.

Example 9

Figure 6:
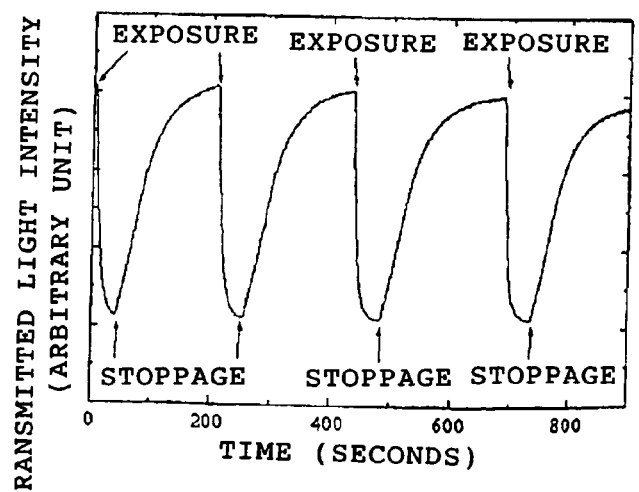
FIG. 6 shows changes over time in the transmitted light intensity of the hydrogen gas detecting material coated on 100 μm thick polyethylene terephthalate (PET) when an operation for exposure to a hydrogen gas and stoppage of the exposure was performed repeatedly.

Changes over time in the transmitted light intensity were examined when an operation involving exposure to a hydrogen gas and its stoppage was performed a plurality of times under the same measuring conditions as in Example 1 for the hydrogen gas detecting material coated on the 100 μm PET sheet in Example 6. The results are shown in FIG. 6. The hydrogen gas detecting material restored transmittance when the hydrogen gas was stopped, namely, when the hydrogen gas was no more existent in the surroundings. Thus, the light absorption characteristics of the hydrogen gas detecting material were found to be reversible in response to the hydrogen gas. When the operation involving exposure to the hydrogen gas and its stoppage was performed repeatedly, a decrease in and the restoration of the transmittance appeared recurrently. Thus, the hydrogen gas detecting material can detect a hydrogen gas repeatedly.

INDUSTRIAL APPLICABILITY

As described in detail above, the present invention relates to an optical hydrogen gas detecting material, and the coating method. The hydrogen gas detecting material of the present invention comprises a thin film of tungsten oxide having palladium deposited as a catalytic metal on the surface thereof. An inexpensive polymeric material can be used as a substrate coated with this thin film. The coating method of the present invention enables coating on many types of substrates, and makes it possible to produce tapes, sheets or test papers for detecting the leakage of a hydrogen gas, as well as hydrogen gas detecting sensors. The resulting products can be expected to find use in the monitoring of a hydrogen gas produced in a hydrogen production plant, the monitoring of leakage of a hydrogen gas in a fuel cell, a hydrogen storage tank or piping for fuel cell vehicles, and the monitoring of a hydrogen gas used or generated during a purification, combination or synthesis process in metal, chemical, foodstuff or pharmaceutical factories. The present invention is useful for providing a coating method for a hydrogen gas detecting material which is indispensable to technologies for commercialization of next-generation hydrogen energy, and which ensures safety.

The invention claimed is:
1. A hydrogen gas detecting material comprising: amorphous tungsten oxide which is shaped as a thin film, wherein
the tungsten oxide is coated on a surface of a substrate by a sputtering method and a temperature of the substrate during coating is set at room temperature,
the substrate is transparent or translucent to visible light, and a change in a transmittance of the hydrogen gas detecting material due to adsorption of hydrogen is 50% or more.

2. The hydrogen gas detecting material according to claim 1, wherein the thin film of the tungsten oxide is 1 μm or less in thickness.

3. The hydrogen gas detecting material according to claim 1, having a stacked structure comprising palladium and the tungsten oxide.

4. The hydrogen gas detecting material according to claim 1, wherein the tungsten oxide is coated, with a pressure of oxygen being controlled.

5. A coating method for the hydrogen gas detecting material according to claim 1, comprising using a sputtering method at a controlled oxygen pressure.

6. The hydrogen gas detecting material according to claim 1, wherein the substrate comprises a material selected from the group consisting of polycarbonate, polyethylene, polyethylene terephthalate (PET), polypropylene, and polyvinylidene chloride.

* * * * *